United States Patent [19]

Fulford et al.

[11] Patent Number: Plant 7,589

[45] Date of Patent: Jul. 16, 1991

[54] APPLE TREE— FULFORD VARIETY

[76] Inventors: Noel G. Fulford; Keith A. Fulford, both of Southland Rd., Hastings, New Zealand

[21] Appl. No.: 410,637

[22] Filed: Sep. 21, 1989

[51] Int. Cl.[5] ..... A01H 5/00

[52] U.S. Cl. ..... Plt./34

[58] Field of Search ..... Plt./34

[56] References Cited

U.S. PATENT DOCUMENTS

P.P. 3,637 10/1974 McKenzie ..... Plt. 34

P.P. 6,172 5/1988 Creech ..... Plt. 34

P.P. 6,955 8/1989 Kiddle ..... Plt. 34

OTHER PUBLICATIONS

Good Fruit Grower, Apr. 1, 1989 edition, Unspecified page.

*Primary Examiner*—Howard J. Locker

*Attorney, Agent, or Firm*—Waters & Morse

[57] ABSTRACT

A discovery of a new apple tree, specifically a mutation of the Kidd or Gala variety, is disclosed. The new apple variety is medium to dark red in color.

1 Drawing Sheet

SUMMARY OF THE INVENTION

The new variety in the present application is a mutation of the Kidd or Gala variety (U.S. Plant Pat. No. 3,637), which we found during 1983 as a single bud sport or limb mutation among trees growing in the Omahuri Orchard in Hastings, New Zealand. We recognized the distinctive coloring of the fruit and other attributes of the variety which were different from the Kidd or Gala apple tree. Asexual reproduction of our discovery was first performed during 1983. The new variety has been named the Fulford variety. Asexual reproduction has shown that the unique combinations of characteristics and distinctive coloring remain true in successive propagations.

BRIEF DESCRIPTION OF THE PHOTOGRAPHIC ILLUSTRATION

The accompanying photograph displays the foliage and fruit of a typical specimen of the present discovery. The color representation is as reasonably close to the live specimen as is possible in illustrations of this kind.

DETAILED DESCRIPTION OF THE PLANT

The following is a detailed description of my new variety with color designations where appropriate. The color terminology is in accordance with the Pantone color system the Pantone Color Formula Guide, 747XR, 1987-1988, and all such designations are Pantone color codes.

In comparison with the Gala (Kidds D-8) variety, U.S. Plant Pat. No. 3,637, the bloom dates and fruit harvest dates are approximately the same, although the fruit of the present variety may be ready for picking slightly earlier or slightly later than the Gala (Kidds D-8), depending on the season. Testing in the Hawkes Bay area of New Zealand, indicated a bloom date of Oct. 15, 1989 and a harvest data of Feb. 15, 1990. The flower color of the new variety is a darker pink in the center than the Gala (Kidds D-8). The fruit yield is approximately Ten Percent (10%) less than the Gala (Kidds D-8). The keeping quality is good but is slightly less than the Gala (Kidds D-8). The fruit of the new variety is somewhat softer than the Gala (Kidds D-8)

and has lower soluble solids at the same level of maturity. The new variety is an annual bearer of fruit.

As for tree characteristics, the bark is substantially the same as the Gala (Kidds D-8) variety, but the tree has flatter branch angles and is slightly less vigorous than the Gala (Kidds D-8).

The color of the fruit is a substantially brighter red than the Gala (Kidds D-8) variety, with the red color being distributed uniformly over the fruit. The color of the new variety is different from the Scarlet Gala variety (U.S. Plant Pat. No. 6,172) in that the Scarlet Gala variety has a light stripe blending to a bright red blush over a cream yellow color. The new variety is a uniform, bright red and has no stripe at all.

The specimens described below were tested at the DSIR Research Orchard, Havelock North, New Zealand.

Tree: Moderately vigorous; spreading; with predominance of bearing on spur.

Dormant one year old shoot: Medium pubescence on upper half; medium thickness; moderate number of lenticels; predominantly reddish brown on the sunny side; pointed bud tips; fruit buds (on spurs) conically shaped.

Flower: Bud color is deep rose just prior to opening; the beginning of flowering (when 10% of the flowers have opened) is early; the flower shape is slightly cupped or flat when observed at the start of anther dehiscence; pressed flat, the flowers are of medium size with petal margins free.

Leaf: General pose of the leaf is upwards; medium in size, 80 mm (millimeters) in length, 40 mm in width for fully expanded leaf; the length/width ratio of blades being medium; cross sectional shape is unfolded; margins show both crenate and serrate indentation; moderate glossiness of upper leaf surface; moderate pubescence on lower leaf surface; petiole length is longer than average; stipule size is moderate.

Fruit: Typically moderate in size, averaging 60 mm (millimeters) in length and 70 mm in breadth; ellipsoid in shape; symmetrical in cross section; little or no ribbing with moderate crowning at the distal end; the aperture of the eye is typically closed; medium sepal length; the basin depth (eye end) is moderate while the width is narrow; ribbing in the basin area is either absent or weak; the skin is smooth and is absent bloom; the skin is thick and has little tendency towards greasiness; the ground color of the skin is yellow and over color (red) is present overall; the over color is solid flush; russet appearance is slight or weak and is found typically around the stalk cavity; lenticles are small; the flesh is firm and yellowish with a fine texture; juicy with moderate to high sweetness; long and narrow "Y" shaped calyx tube; core line in cross section (median through locules) is moderately distinct with the apertures of the locules open.

*Maturity.*—Ripening for eating is early, approximately 10 days earlier than Cox's Orange Pippin; maturity for picking is approximately 3 days later than Cox's Orange Pippin.

*Seed.*—Seeds are small and brown in color when dried.

*Color.*—The fruit has a pleasing and fairly uniform red appearance. The red varies moderately from a medium shade (Pantone 186C, 193C, 199C and 200C) to a deeper color (Pantone 187C and 201C).

The leaf color is typical and varies somewhat. The leaf color is best typified as a dark green (Pantone 3302C, 3308C, 3435C and 350C). Lighter greens may occur on portions of the leaf or leaf edge and have been observed only as an inferior coloration (Pantone 364C).

Resistance to:

*Apple black spot.*—Good.

*Powdery mildew.*—Good to highly resistant.

*Glomerella cingulate.*—Susceptible.

*Wooly aphid.*—Good to highly resistant.

*Red mite.*—Good.

*Leaf roller.*—Good.

Stalk: Thick; moderately long; stalk cavity is deep and of medium width.

I claim:

1. A new and distinct variety of apple tree which is a mutation of the Kidd or Gala variety (U.S. Plant Pat. No. 3,637) substantially as shown and described, characterized by an overall bright red color.

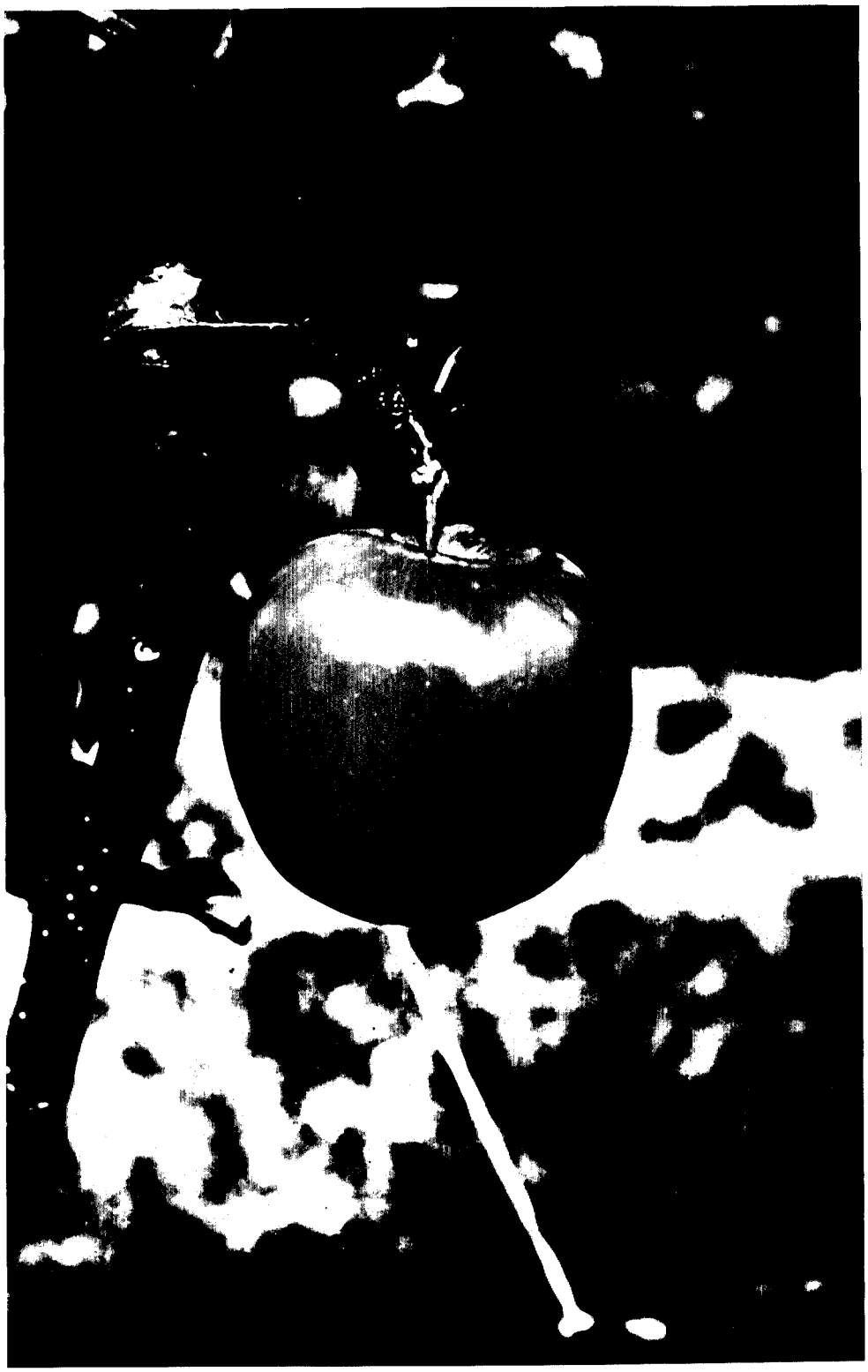

* * * * *